US00PP29403P2

(12) United States Plant Patent
Thompson

(10) Patent No.: US PP29,403 P2
(45) Date of Patent: Jun. 19, 2018

(54) RASPBERRY PLANT NAMED 'PBBRASP1351'

(50) Latin Name: ***Rubus idaeus* L.**
Varietal Denomination: PBBrasp1351

(71) Applicant: Pacific Berry Breeding, LLC, Salinas, CA (US)

(72) Inventor: Ellen Thompson, Watsonville, CA (US)

(73) Assignee: Pacific Berry Breeding, Salinas, CA (US)

( * ) Notice: Subject to any disclaimer, the term of this patent is extended or adjusted under 35 U.S.C. 154(b) by 0 days. days.

(21) Appl. No.: 15/731,005

(22) Filed: Apr. 5, 2017

(51) Int. Cl.
*A01H 5/08* (2018.01)

(52) U.S. Cl.
USPC ..... Plt./204

(58) Field of Classification Search
USPC ..... Plt./204
See application file for complete search history.

*Primary Examiner* — Annette H Para
(74) *Attorney, Agent, or Firm* — King IP Law; Joshua King

(57) ABSTRACT

The present application relates to new and distinct cultivar of primocane-fruiting raspberry named 'PBBrasp1351'. The new variety reliably provides balanced heavy crop load on both primocanes and floricanes, with large, glossy, conic fruits of unique peach-yellow color, with loose adherence to the receptacle and which maintain size throughout harvest. Plants possess high vigor and produce high numbers of spawn. Improved resistance to yellow rust (*Phragmidium rubi-idaei*) and field tolerance to Raspberry Bushy Dwarf Virus (RBDV) and *Phytophthora* root rot has been observed.

5 Drawing Sheets

Latin name of the genus and species of the plant claimed: *Rubus idaeus* L.

Variety denomination: 'PBBrasp1351'.

BACKGROUND AND SUMMARY

The new primocane-fruiting raspberry cultivar designated as 'PBBrasp1351' is described herein. Botanically known as *Rubus idaeus* L., this new variety resulted from a hand-pollinated cross of female parent 'Pacific Gema' (U.S. Plant Pat. No. 28,080), a patent-pending release from the same program, and the unpatented male parent '1108'. Pollination occurred in April 2012 and seeds from this controlled cross were subsequently harvested, cleaned, germinated, and established as seedlings in spring 2013 in Watsonville, Calif., Santa Cruz County, USA.

'PBBrasp1351' was first identified in a substrate block, where seedlings had individually been planted into 3 liter pots, in September 2013 in Watsonville, Calif. This selection was first propagated asexually by crown division (of the original potted mother-plant) in autumn 2013 in Watsonville, Calif. The crown on the original plant was parted into basal cane pieces (approximately 15 cm long) with root attached and planted into soil, in a selection plot elsewhere on the farm, resulting in a 10-fold increase in plant material. Harvest and postharvest data were collected from this larger plot of 'PBBrasp1351' for two years, from 2014 through 2016.

In January 2014, additional root pieces from the original mother-plant were planted into an on-site greenhouse. Two actively growing etiolated shoots were forced from roots, transplanted and potted. Once established, these shoots were sent to Lafayette, Oreg., USA, where vegetative material was explanted and established in vitro for micropropagation. Subsequent asexual propagation was done on-site in Watsonville, Calif. and, along with tissue-cultured plantlets, 'PBBrasp1351' was evaluated extensively over the next several years for performance and genetic stability.

The present cultivar, 'PBBrasp1351' offers many advantages over the existing, patent-pending cultivar and red-fruited maternal parent, 'Pacific Gema' (U.S. Plant Pat. No. 28,080) and the yellow-fruited paternal parent '1108'. The most distinct characteristic 'PBBrasp1351' is the color, which is unlike either parent. 'PBBrasp1351' has an intermediate color, with peach-colored overtones and yellow-colored undertones. Often, berries of 'PBBrasp1351' appear to be two-tone, which is unique for raspberry. The unique color offers significant advantages to marketers who seek methods to distinguish commodity products. Average fruit size of 'PBBrasp1351' is considerably larger than both parents. Berries detach easily from the receptacle, which is similar to parent '1108', yet much easier than 'Pacific Gema'. Fruits of 'PBBrasp1351' are broadly-conic in shape (versus the narrow conic shape of 'Pacific Gema' and '1108'). Yield of 'PBBrasp1351' is also much greater than 'Pacific Gema' and '1108', on average, due to its higher vigor and larger fruit size. The ease of fruit detachment and improved yield offers significant advantages to growers, who require fast picking speeds and lighter fruit color, combined with glossiness which helps to extend shelf life of the fruit (by appearing to stay fresher for a longer period of time). The larger, broadly-conic berries help growers fill baskets more quickly, leading to increased harvest efficiency. Root vigor, subsequent cane vigor, and floricane budbreak for 'PBBrasp1351' is superior to 'Pacific Gema' and '1108'.

In contrast to the unpatented male parent '1108', the cultivar is significantly greater in vigor, plant fitness and offers larger fruit. In particular, the amount of suckers that 'PBBrasp1351' produces is two-fold of its paternal parent. This improvement is of significant importance to growers, who rely upon the regenerative ability of suckers, in order to guarantee subsequent crops. The unique two-tone color of 'PBBrasp1351' is distinct, and therefore desirable, in contrast to that of the yellow-fruited male parent (yellow raspberries are already in the commercial trade). All patented previous releases from this program, including 'Pacific Deluxe' (U.S. Plant Pat. No. 21,074), 'Pacific Royale' (U.S. Plant Pat. No. 21,536) and 'Pacific Majesty' (U.S. Plant Pat. No. 47,306) have red fruit color (as is standard for raspberries). This further indicates 'PBBrasp1351' as a unique variety. Thus, these characteristics help define 'PBBrasp1351' as a new and distinct cultivar of primocane-fruiting raspberry. 'PBBrasp1351' may be recognized by its unique fruit color, high vigor, strong suckering habit, superior floricane budbreak, large broadly-conic berries of peach-yellow color and high gloss, and which consistently yield more than existing varieties within the same program.

BRIEF DESCRIPTION OF THE PHOTOGRAPHS

Figure 1:
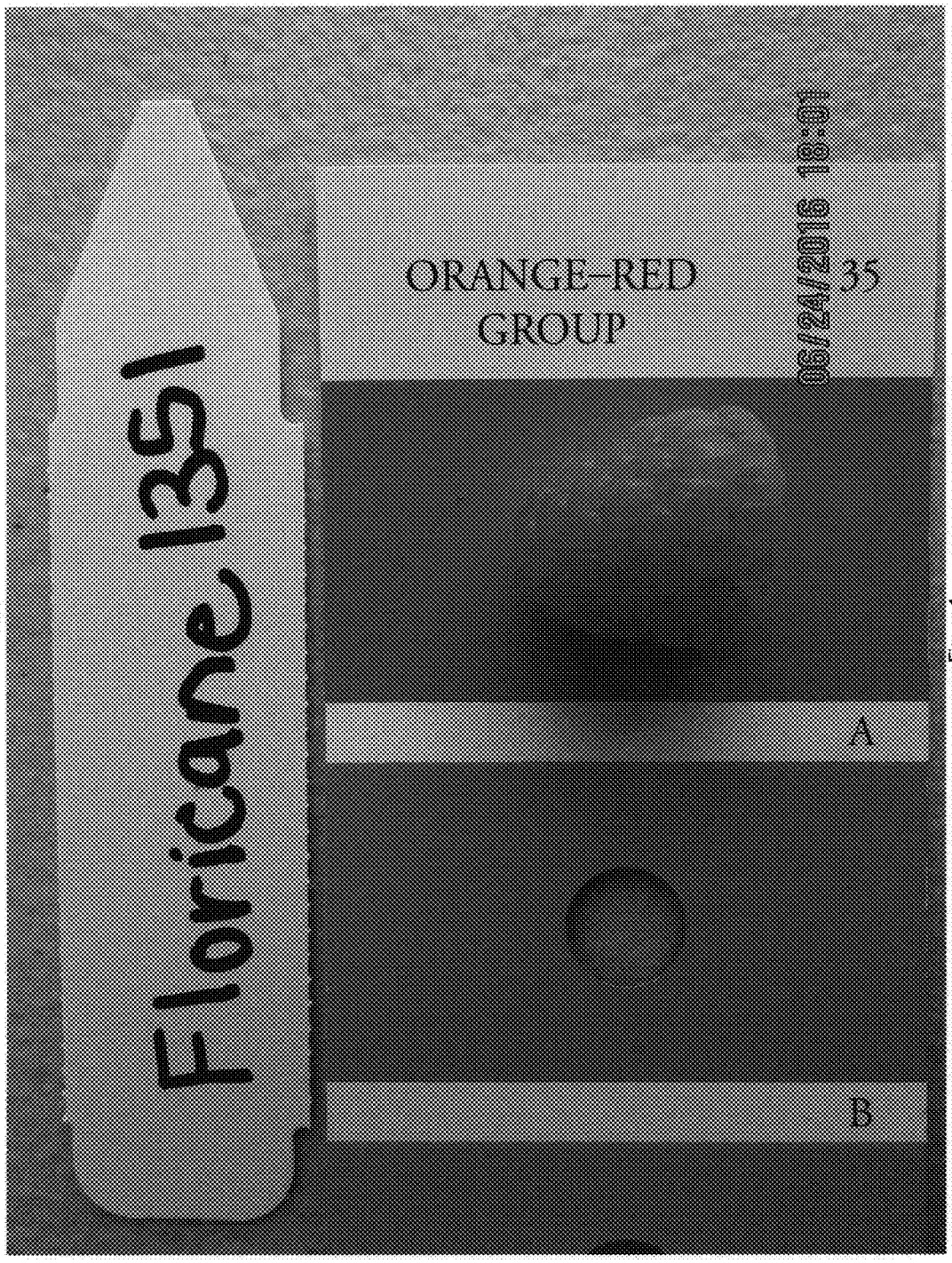
FIG. 1 is a photograph showing the fresh fruit overtone of raspberry cultivar 'PBBrasp1351'.
Figure 2:
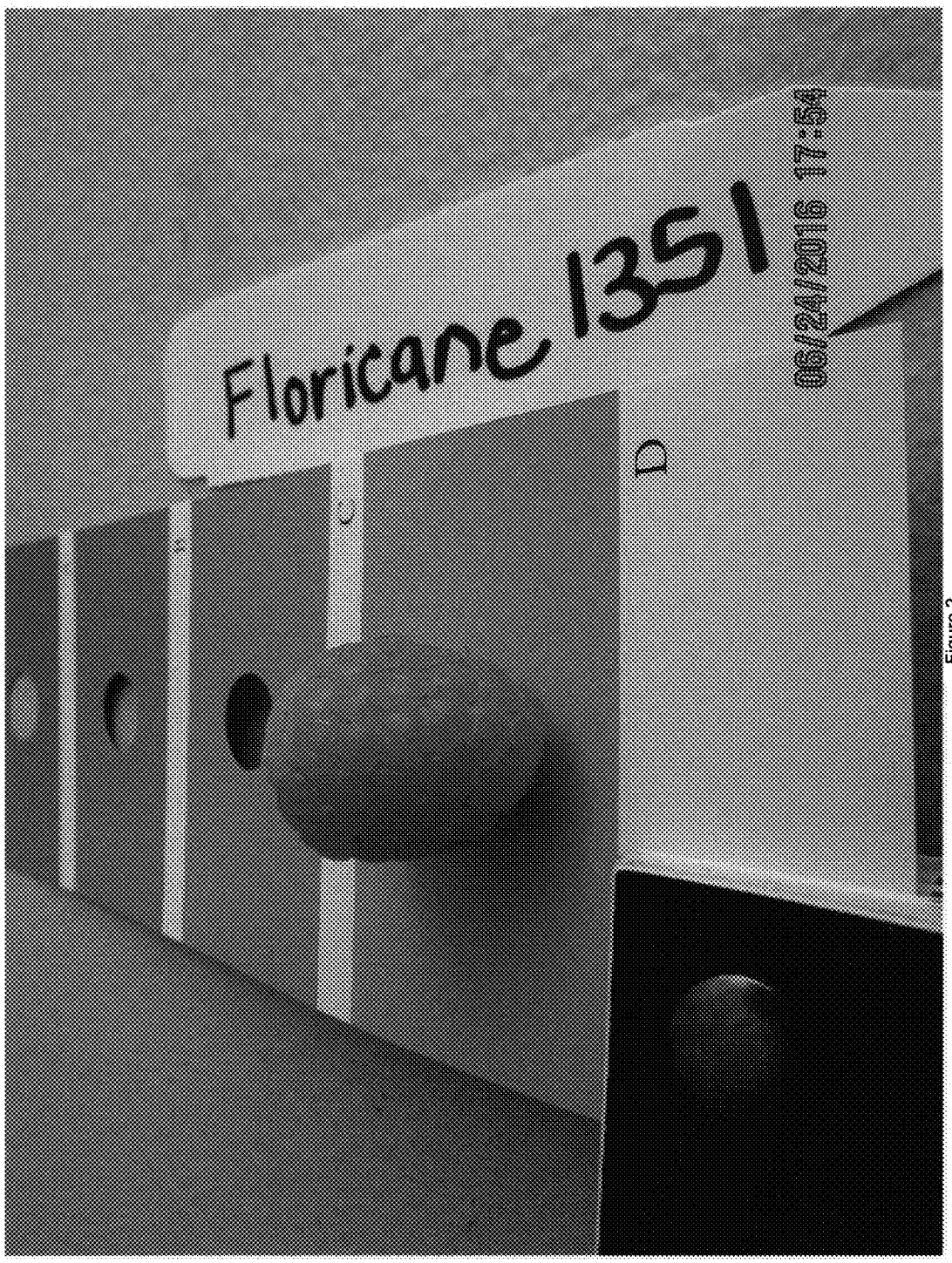
FIG. 2 is a photograph showing the fresh fruit undertone of raspberry cultivar 'PBBrasp1351'.
Figure 3:
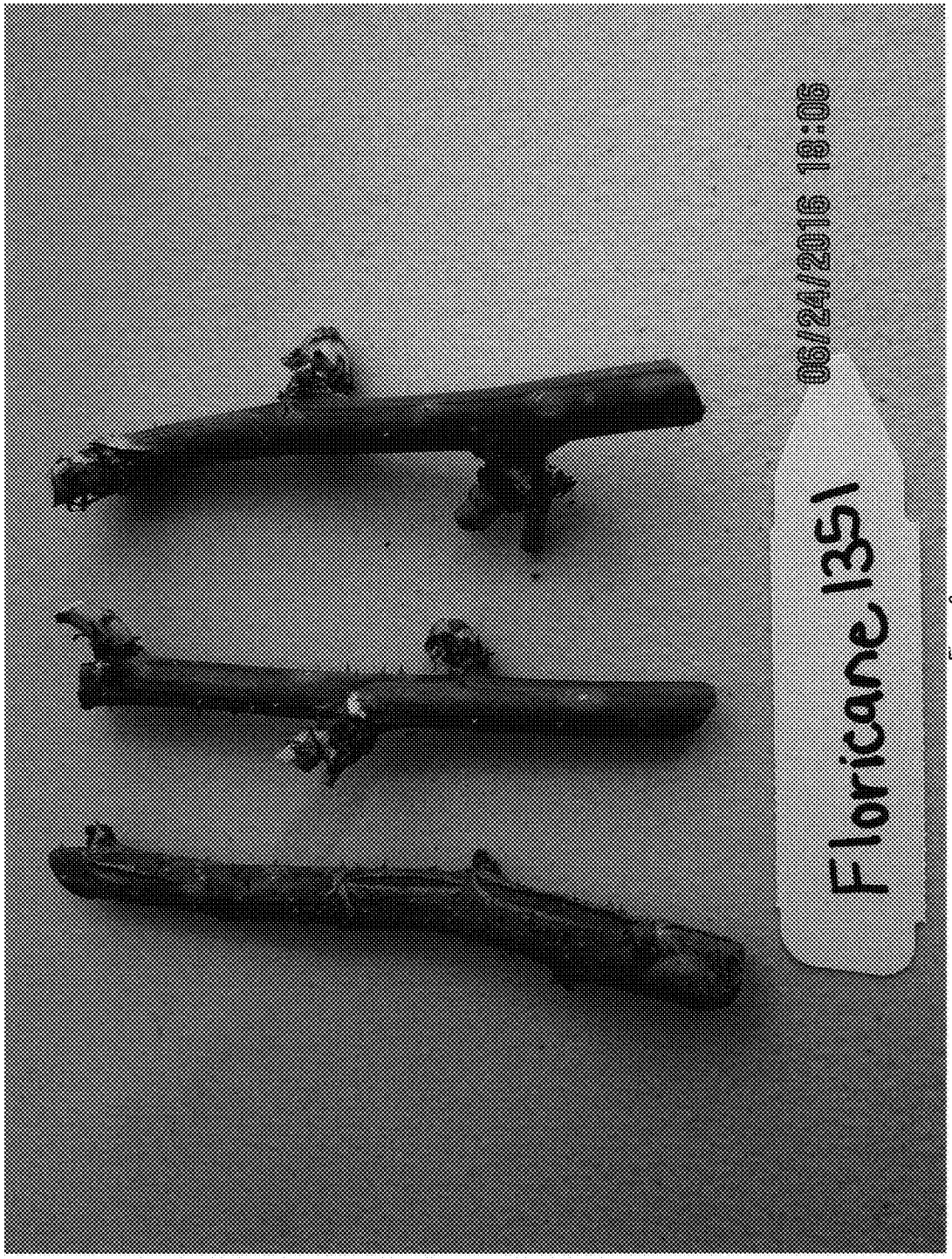
FIG. 3 is a photograph showing the floricane and spine color of raspberry cultivar 'PBBrasp1351'.
Figure 4:
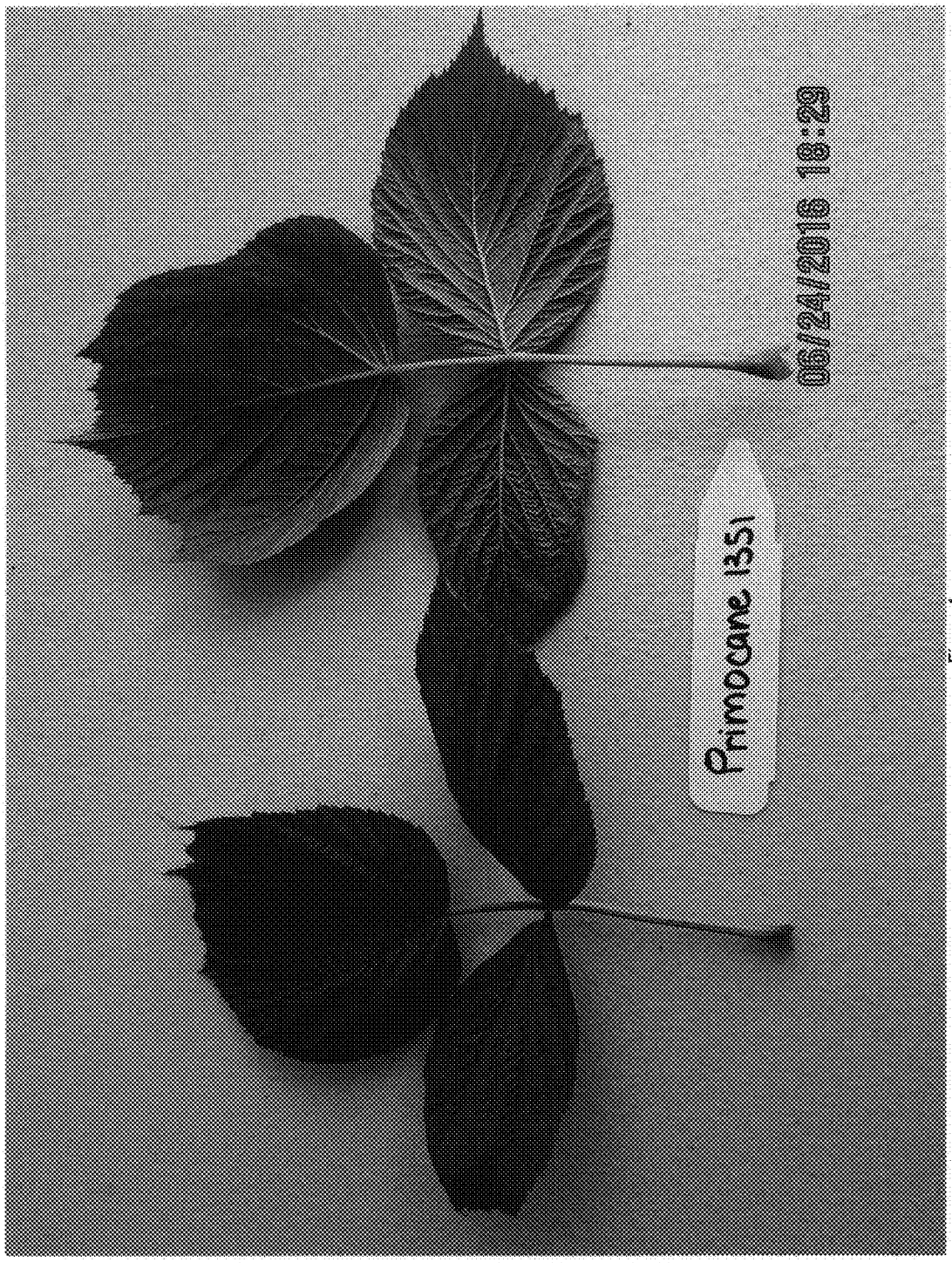
FIG. 4 is a photograph displaying leaf size and morphology of raspberry cultivar 'PBBrasp1351'.
Figure 5:
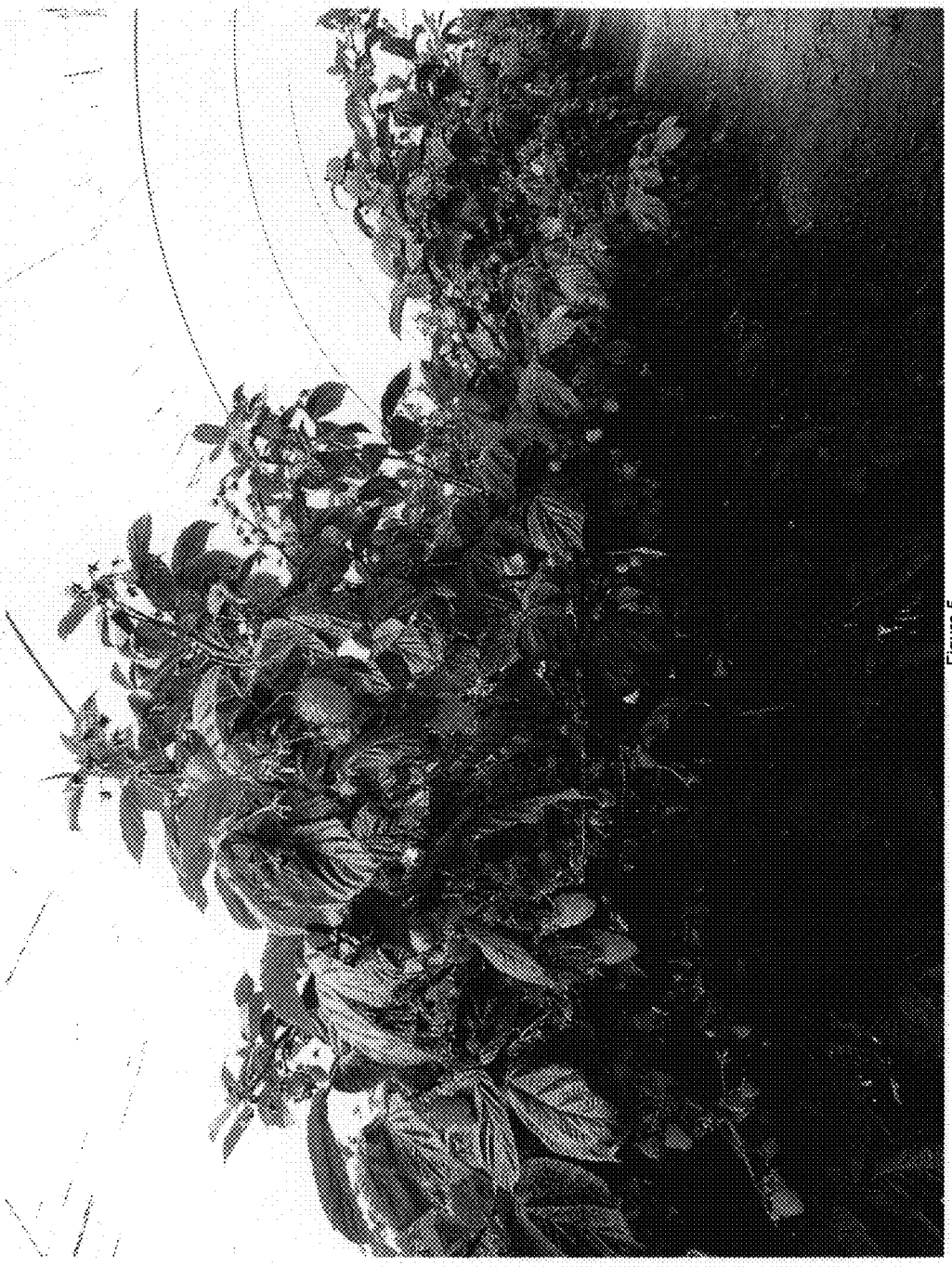

FIG. 5 photograph displaying the vigor, canopy, primocane crop load and architectural habit of raspberry cultivar 'PBBrasp1351'.

DETAILED DESCRIPTION

Note: statements of characteristics herein represent exemplary observations of the cultivar herein and will vary depending on time of year, location, annual weather, etc.

Cultivar name: 'PBBrasp1351'.

Classification:

*Family*.—Rosaceae.

*Botanical name*.—*Rubus idaeus* L.

*Common name*.—Raspberry.

Parentage:

*Female parent*.—'Pacific Gema' (U.S. Plant patent application Ser. No. 14/544,823, filed Feb. 24, 2015).

*Male parent*.—'1108' (unpatented). As noted above, the present cultivar, 'PBBrasp1351' offers many advantages over the red-fruited maternal parent, 'Pacific Gema', and the yellow-fruited paternal parent '1108'. The most distinct characteristic of 'PBBrasp1351' is the color, which is unlike either parent. 'PBBrasp1351' has an intermediate color, with peach-colored overtones and yellow-colored undertones. Often, berries of 'PBBrasp1351' appear to be two-tone, which is unique for raspberry. The unique color offers significant advantages to marketers who seek methods to distinguish commodity products. Average fruit size of 'PBBrasp1351' is considerably larger than both parents. Berries detach easily from the receptacle, which is similar to parent '1108', yet much easier than 'Pacific Gema'. Fruits of 'PBBrasp1351' are broadly-conic in shape (versus the narrow conic shape of 'Pacific Gema' and '1108'). Yield of 'PBBrasp1351' is also much greater than 'Pacific Gema' and '1108', on average, due to its higher vigor and larger fruit size. The ease of fruit detachment and improved yield offers significant advantages to growers, who require fast picking speeds and lighter fruit color, combined with glossiness which helps to extend shelf life of the fruit (by appearing to stay fresher for a longer period of time). The larger, broadly-conic berries help growers fill baskets more quickly, leading to increased harvest efficiency. Root vigor, subsequent cane vigor, and floricane budbreak for 'PBBrasp1351' is superior to 'Pacific Gema' and '1108'. In contrast to the unpatented male parent '1108', the present invention is significantly greater in vigor, plant fitness and offers larger fruit. In particular, the amount of suckers that 'PBBrasp1351' produces is two-fold of its paternal parent. This improvement is of significant importance to growers, who rely upon the regenerative ability of suckers, in order to guarantee subsequent crops. The unique two-tone color of 'PBBrasp1351' is superior to that of the yellow-fruited male parent.

Growing location for the observations herein: Watsonville, Calif., USA.

Time of year (season): Spring 2016 for floricanes; Summer 2016 for primocanes.

Age of plants used for this discussion: Crown age of about 2 years; floricane age=18 months; primocane age=7 months.

Age of plants used for the photographs in the figures: Crown age of about 3 years and a cane age of about 4-8 months.

Type of greenhouse covering or growing structure, or field: High tunnel over field-grown plants.

Light: Natural. Color terminology refers to The R.H.S. Colour Chart, Royal Horticultural Society, Fifth Edition, London, United Kingdom (2007). Observations for floricanes herein were made in spring 2016. Observations for primocanes herein were made in summer 2016.

Plant:

*Form/shape*.—Vase.

*Growth habit*.—Erect.

*Height*.—2.1 m as the plot average, as measured from cane base to apex.

*Spread*.—0.4 m as measured from terminal leaflet tip to terminal leaflet tip.

*Propagation methods*.—Division.

*Time to initiate and develop roots*.—28 days.

*Root description*.—Fibrous. Generally of medium diameter with a smooth, glossy texture.

Primocanes:

*Cane diameter*.—Base — 1.3 cm|Middle — 1.1 cm|Tip — 0.7 cm.

*Cane length*.—82.5 cm, as measured from cane base to apex.

*Number of node per cane*.—40.

*Internode length*.—Base — 6.7 cm|Middle — 8.9 cm|Tip — 3.5 cm.

*Number of canes/hill*.—7 to 8.

*Cane color*.—Lower cane — RHS N144D|Upper cane — RHS 183C.

*Spines*.—Present.

*Spine density*.—Base — 9/cm$^2$|Middle — 1/cm$^2$|Tip — 2/cm$^2$.

*Spine shape*.—Acuminate.

*Spine length*.—0.07 cm.

*Spine width*.—0.02 cm.
*Spine apex descriptor*.—Acuminate.
*Spine color*.—RHS 183B.
*Vegetative bud shape*.—Rounded.
*Vegetative bud length*.—1.5 cm.
*Vegetative bud diameter* (*base*).—0.8 cm.
*Vegetative bud diameter* (*tip*).—0.09 cm.
*Vegetative bud color*.—Lower bud — RHS 143B|Upper bud — RHS145D.

Floricanes:
*Cane diameter*.—Base — 1.3 cm|Middle — 1.1 cm|Tip — 1.2 cm.
*Cane length*.—96.8 cm.
*Number of nodes per cane*.—22. Internode Length: Base — 4.3 cm|Middle — 6.9 cm|Tip — 10.9 cm.
*Cane color*.—Lower Cane — RHS-175C|Upper Cane — RHS N170A.
*Spines*.—Present. Spine density: Base — 5/cm$^2$|Middle — 4/cm$^2$|Tip — 2/cm$^2$. Spine shape: Acuminate. Spine length: 0.3 cm. Spine width: 0.05 cm. Spine apex descriptor: Acuminate. Spine color: RHS N167C.
*Reproductive bud shape*.—Rounded.
*Reproductive bud length*.—1.9 cm.
*Reproductive bud diameter* (*base*).—0.8 cm.
*Reproductive bud diameter* (*tip*).—0.1 cm.
*Reproductive bud color*.—RHS 143C.
*Reproductive bud texture*.—Pubescent.
*Winter hardiness*.—Unknown outside of USDA Hardiness Zone 9b (Watsonville, Calif.). This cultivar is best adapted to the mild coastal conditions of California.
*Drought/heat tolerance*.—Pollen viability and fruit quality of raspberry generally begins to decline above 30° C. This is consistent with observations of 'PBBrasp1351'. Raspberries are generally not drought tolerant, and 'PBBrasp1351' has not been tested in unirrigated plots.

Leaves:
*Complete leaf*.—Length: 22.4 cm. Width: 19.8 cm. Number of leaflets: 3.
*Terminal leaflet*.—Size. Length: 12.9 cm. Width: 8.3 cm. Length/Width ratio: 1.6 cm. Leaf shape of apex: Acuminate. Leaf shape of base: Cordate. Leaf margin: Serrate. Leaf texture: Rigid interveinal puckering. Number of serrations per leaf: 99 serrations. Leaf shape of serrations: Flexuous — Flexuous. Leaf color: Upper Surface: RHS N137B. Lower Surface: RHS N138C. Leaf venation pattern: Palmate. Leaf venation color: Upper surface: RHS N144D. Lower surface: RHS N144D. Leaf pubescence density: Present on underside only; moderate. Color of leaf pubescence: RHS N138C. Shape of leaf in cross-section: Oval. Number of leaflets/leaf: Primocane: 3-5 Floricane: 3. Interveinal blistering within leaf: Present. Leaf glossiness: Matte.
*Primocane leaves*.—Petiole length: 6.5 cm. Petiole diameter: 0.2 cm. Petiole Color: Upper: RHS 144B for shaded areas; RHS 184C for sun-exposed areas. Lower: RHS 144D. Rachis length: 2.6 cm. Stipule length: 2.2 cm. Stipules per leaf: 2. Stipule Width: 0.007 cm. Stipule Color: Upper Surface: RHS 184A. Lower Surface: RHS 144A.
*Terminal leaflet*.—Length: 12.9 cm. Width: 8.7 cm. Rachis length: 2.9 cm.
*Distal lateral leaflet*.—Length: 8.9 cm. Width: 5.7 cm. Petiolule length: Sessile.
*Basal lateral leaflet*.—Length: 11.3 cm. Width: 7.1 cm. Petiolule length: Sessile.
*Floricane leaves*.—Petiole length: 4.2 cm. Stipule length: 0.7 cm. Stipules per leaf: 2. Stipule Width: 0.008 cm. Stipule Color: Upper surface: RHS 144A. Lower surface: RHS 144A.
*Terminal leaflet*.—Length: 12.9 cm. Width: 8.3 cm. Rachis length: 2.6 cm. Distal lateral leaflet: Not Present. Length: N/A. Width: N/A.
*Petiolule*.—Length: N/A. Diameter: N/A. Color: N/A.
*Basal lateral leaflet*.—Length: 10.6 cm. Width: 4.6 cm.
*Petiolule*.—Length: Sessile. Diameter: N/A. Color: Upper: N/A. Lower: N/A.

Flowers:
*Time of flowering* (*50% of plants at first flower*): Approximately 88 days after planting (on primocanes).
*Flower size*.—Length: 1.1 cm. Diameter: 0.8 cm.
*Fragrance*.—Light floral fragrance.
*Peduncle*.—Length: 8.0 cm. Diameter: 0.3 cm. Color: RHS 144B. Pubescence: None. Texture: Smooth, with spines.
*Perianth*.—Flowering trusses shape: Truncate.
*Petals*.—Color: Upper — RHS 157B|Lower — RHS 157B. Number per flower: 5 petals. Shape: Obovate. Length: 0.8 cm. Width: 0.3 cm. Apex descriptor: Rounded. Base Descriptor: Cuneate. Margin descriptor: Entire. Texture: Smooth with visible striations.
*Sepals*.—Quantity: 5 sepals. Length: 1.0 cm. Width: Base — 0.4 cm|Mid — 0.3 cm|Tip — 0.08 cm. Color: RHS 144D for sepal base and mid-section; RHS 183B for sepal tip. Apex descriptor: Acuminate. Margin descriptor: Entire. Texture: Pubescent.
*Pedicel*.—Color: RHS 143C. Length: 2.4 cm. Diameter: 0.1 cm.

Reproductive organs:
*Self-fertile*.—Yes.
*Male*.—
*Stamen number*.—111.
*Filament*.—Length: 0.5 cm. Diameter: 0.01 cm. Color: RHS 155A.
*Anther*.—Length: 0.05 cm. Diameter: 0.03 cm. Color: RHS 199C.
*Pollen*.—Color: RHS 199C. Amount: Moderate.
*Female*.—
*Style*.—Length: 0.4 cm. Diameter: 0.006 cm. Color: RHS 157C.
*Stigma*.—Length: 0.03 cm. Diameter: 0.008 cm. Color: RHS 158A.
*Ovary*.—Length: 0.01 cm. Diameter: 0.07 cm. Color: N144D.

Fruit:
*Predominant shape*.—Broad Conical.
*Weight* (*g*).—5.4 g.
*Length*.—2.8 cm.
*Width*.—Base — 2.9 cm|Mid — 1.7 cm|Tip — 1.3 cm.
*Length/width ratio*.—1.42 cm.
*Receptacle*.—Length: 1.7 cm. Diameter: Base — 0.6 cm|Mid — 0.4 cm|Tip — 0.2 cm. Color: RHS 18D.
*Drupelet*.—Length: 0.7 cm. Diameter: 0.4 cm. Number: 102. Weight: 0.06 g.
*Fruit color*.—External: Bicolor RHS 170D and RHS 35A. Internal: RHS 35C.

*Firmness of skin*.—Firm.
*Firmness of flesh*.—Soft.
*Hollow center*.—Yes.
*Number of fruit per node*.—9.
*Time of ripening* (50% *of plants with first fruit*).—134 days after planting, on average.
*Time of fruiting*.—Spring to summer on floricanes; late summer and early autumn on primocanes.
*Type of bearing*.—Remontant.
*Fruit yield*.—19,453 lb/a, on average.
*Average brix*.—9.9.
*Typical market use*.—Fresh.
*Keeping quality*.—Excellent.
*Shipping quality*.—Excellent.

Pest and disease resistance: PBBrasp1351 shows resistance to yellow rust (*Phragmidium rubi-idaei*), a common fungal disease under commercial conditions. PBBrasp1351 has exhibited field tolerance to Raspberry Bushy Dwarf Virus (RBDV) and *Phytophthora* root rot.

What is claimed is:

1. A new and distinct cultivar of Raspberry plant named 'PBBrasp1351' as described and shown herein.

* * * * *